United States Patent
Noda

(10) Patent No.: US 10,942,194 B2
(45) Date of Patent: Mar. 9, 2021

(54) AUTOMATIC ANALYZER

(71) Applicant: HITACHI HIGH-TECHNOLOGIES CORPORATION, Tokyo (JP)

(72) Inventor: Takayuki Noda, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 315 days.

(21) Appl. No.: 15/750,957

(22) PCT Filed: Jul. 11, 2016

(86) PCT No.: PCT/JP2016/070421
§ 371 (c)(1),
(2) Date: Feb. 7, 2018

(87) PCT Pub. No.: WO2017/033597
PCT Pub. Date: Mar. 2, 2017

(65) Prior Publication Data
US 2018/0224477 A1   Aug. 9, 2018

(30) Foreign Application Priority Data
Aug. 26, 2015   (JP) .............................. JP2015-166787

(51) Int. Cl.
*G01N 35/10*   (2006.01)
*G01N 35/00*   (2006.01)
(Continued)

(52) U.S. Cl.
CPC ... *G01N 35/1004* (2013.01); *G01N 35/00623* (2013.01); *G01N 33/483* (2013.01);
(Continued)

(58) Field of Classification Search
CPC ......... G01N 35/1004; G01N 35/00623; G01N 35/02; G01N 35/00; G01N 33/483; G01N 35/08; G01N 35/10; G01N 2035/0437
See application file for complete search history.

(56) References Cited

U.S. PATENT DOCUMENTS

| 2010/0161243 A1* | 6/2010 | Nagai | G01N 35/00663 702/25 |
| 2013/0311243 A1* | 11/2013 | Taki | G01N 35/0092 705/7.38 |
| 2015/0204895 A1* | 7/2015 | Yasui | G01N 35/1004 422/64 |

FOREIGN PATENT DOCUMENTS

| JP | 2000-131325 A | 5/2000 |
| JP | 2000-266757 A | 9/2000 |

(Continued)

OTHER PUBLICATIONS

International Search Report PCT/JP2016/070421 dated Oct. 11, 2016.
(Continued)

*Primary Examiner* — Benjamin R Whatley
*Assistant Examiner* — Curtis A Thompson
(74) *Attorney, Agent, or Firm* — Mattingly & Malur, PC

(57) ABSTRACT

An automatic analyzer configured to automatically prevent interruption of an analysis owing to water shortage in use includes a plurality of analysis sections using water supplied from the outside, an operation section for giving operation instructions to the analysis sections, and a control section executing a program for controlling operations of the analysis sections. The control section switches maintenance using water between simultaneous execution and time difference execution for all the analysis sections in accordance with an instruction input through the operation section.

4 Claims, 9 Drawing Sheets

(51) Int. Cl.
G01N 35/04 (2006.01)
G01N 35/02 (2006.01)
G01N 33/483 (2006.01)
G01N 35/08 (2006.01)

(52) U.S. Cl.
CPC ......... *G01N 35/00* (2013.01); *G01N 35/0092* (2013.01); *G01N 35/02* (2013.01); *G01N 35/08* (2013.01); *G01N 35/10* (2013.01); *G01N 2035/0437* (2013.01)

(56) References Cited

FOREIGN PATENT DOCUMENTS

| JP | 2001-228160 A | | 8/2001 | |
|----|---------------|---|--------|---|
| JP | 2001228160 | * | 8/2001 | ............. G01N 35/10 |
| JP | 2010-122123 A | | 6/2010 | |

OTHER PUBLICATIONS

Extended European Search Report received in corresponding European Application No. 16838944.3 dated Feb. 14, 2019.
Chinese Office Action received in corresponding Chinese Application No. 201680045647.3 dated Nov. 29, 2019.

* cited by examiner

AUTOMATIC ANALYZER

TECHNICAL FIELD

The present invention relates to an automatic analyzer including a plurality of analysis sections, configured to change water consumption in accordance with an operation state.

BACKGROUND ART

The automatic blood analyzer as a typical biochemical automatic analyzer is configured to execute a plurality of measurements of samples collected from patients simultaneously. The above-described instrument has its respective parts cleaned so as to prevent the component contained in the sample of a certain patient from influencing the measurement of the sample collected from another patient. Since tap water contains foreign matters and other components that may influence the analysis results, pure water derived from purification through the pure water supply apparatus and the like has been generally used for cleaning purpose.

The automatic analyzer for processing a large number of samples per unit time has the unit operation cycle reduced to be less than several seconds, thus failing to perform sufficient cleaning. Therefore, maintenance for the automatic analyzer is indispensable to prevent accumulation of impurities. Meanwhile, it will take substantial time to carryout the cleaning during the maintenance work. The consumption of pure water for the maintenance tends to be more than the water consumption of the sample measurement.

Generally, the pure water supply apparatus capable of supplying maximum amount of pure water is prepared for introduction of the automatic analyzer in the institution so as to execute the maintenance at any time. However, the automatic analyzer does not always consume the maximum amount of pure water. Considering the use of the pure water supply apparatus in operation for a newly introduced automatic analyzer, a certain user may inquire the manufacturer about the amount of pure water constantly consumed by the automatic analyzer. Another user may interpose the water tank for connection between the pure water supply apparatus and the automatic analyzer so that the water tank stores pure water by the amount required for the limited usage such as the maintenance work.

A certain type of automatic analyzer including a plurality of analysis sections may be configured to individually operate the respective analysis sections. The automatic analyzer of this type avoids water shortage by executing the maintenance work for the respective analysis sections one by one sequentially so as not to exceed the current supply capability of the pure water supply apparatus.

In spite of the above-described measures, the water shortage cannot be necessarily avoided. A difference in water consumption owing to fluctuation in the supply capability of the pure water supply apparatus, and individual differences among the automatic analyzers may cause the water shortage. In the case of using the water tank, there may be the risk of propagation of various bacteria in the stored pure water, requiring the maintenance for the water tank on a regular basis. The water tank and piping may occupy substantial space of the laboratory for inspection.

In the maintenance for the analysis sections of the automatic analyzer in sequence, at the end of the maintenance for the first analysis section, the user has to instruct to start the maintenance for the second analysis section. This inevitably results in troublesome operations.

Patent Literature 1 discloses the method of reducing the water consumption which will be temporarily increased at startup of the analyzer for the purpose of reducing the burden in the situation as described above. The disclosed method is intended to control each execution of the process for the respective sections at startup of the analyzer so that the water consumption does not exceed the required value of water consumption during the operation.

CITATION LIST

Patent Literature

Patent Literature 1: Japanese Unexamined Patent Application Publication No. 2001-228160

SUMMARY OF INVENTION

Technical Problem

The technology as disclosed in Patent Literature 1 is not effective for the maintenance work to be executed after startup of the analyzer. Also, with the technology as disclosed in Patent Literature 1, it is difficult for the user to determine whether the water consumption is suppressed, or the maximum amount of water is available in accordance with the water consumption state of the analyzer.

It is an object of the present invention to provide an automatic analyzer capable of automatically preventing interruption of the analysis owing to water shortage in operation.

Solution to Problem

The present invention employs the structure as described in the claim for solving the above-described problem. This specification includes a plurality of solution to the above problems. For example, the present invention provides an automatic analyzer which includes a plurality of analysis sections using water supplied from the outside, an operation section for giving operation instructions to the analysis sections, and a control section executing a program for controlling operations of the analysis sections. The control section switches maintenance using water between simultaneous execution and time difference execution for all the analysis sections in accordance with an instruction input through the operation section.

Advantageous Effects of Invention

The present invention allows construction of the inspection laboratory that automatically prevents interruption of the analysis owing to water shortage in operation. Objects, structures and advantageous effects other than those described above will be made apparent by the following description of the embodiment.

DESCRIPTION OF EMBODIMENTS

Figure 1:
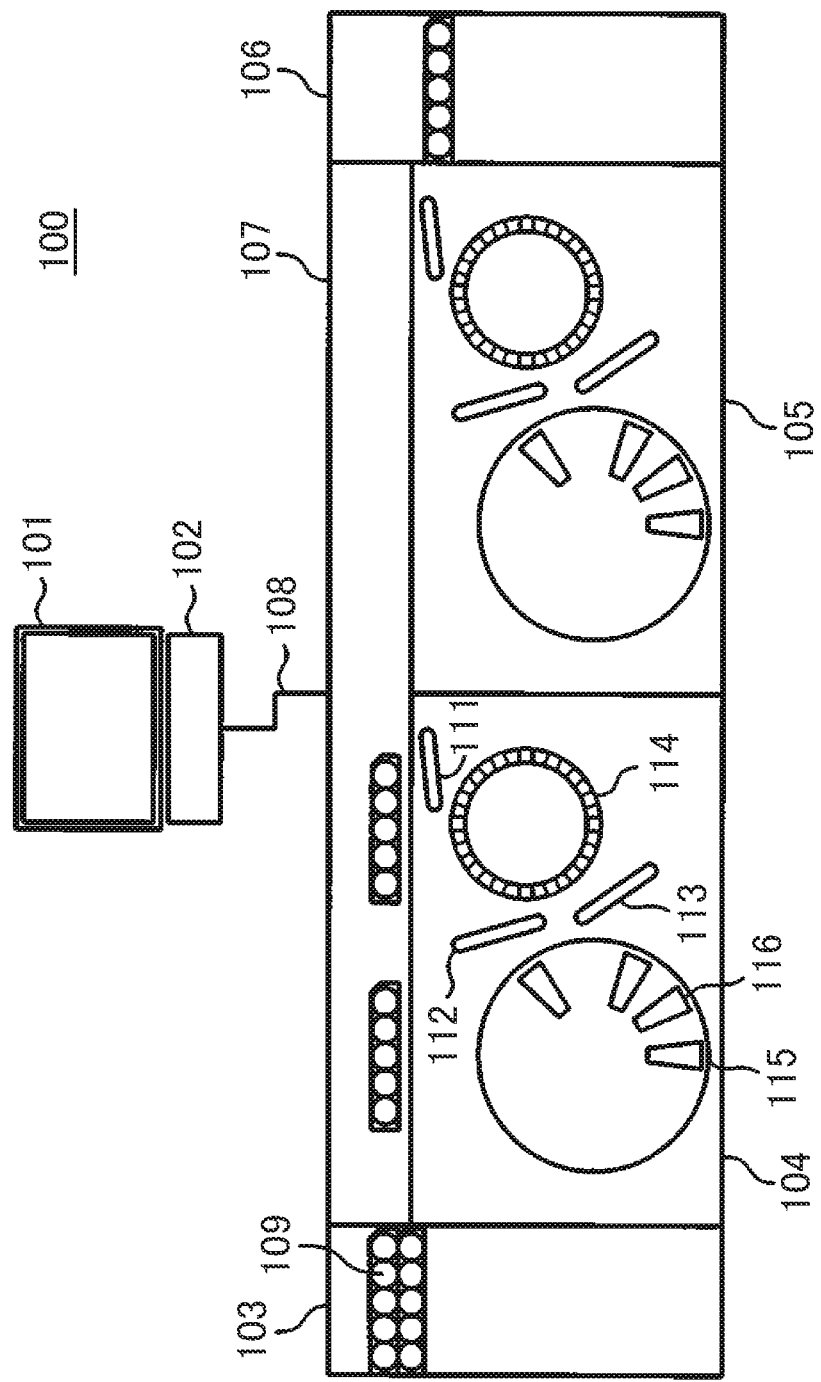
FIG. 1 is a view schematically showing a structure of an automatic analyzer according to an example.

Embodiments according to the present invention will be described referring to the drawings. Embodiments according to the present invention are not limited to examples described below, and may be modified into various forms without departing from the scope of the present invention.

(1) Example 1

(1-1) Structure of Analyzer

FIG. 1 shows an exemplary structure of an automatic analyzer 100. An operation section 102 includes a computer (a CPU, a storage section, an interface) for controlling operations of the automatic analyzer 100 including an analysis section. The CPU functions as a control section for controlling operations of the analysis section through execution of the program. The operation section 102 displays various information on an associated display 101 so as to notify the operator of the state of the automatic analyzer 100. The operation section 102 displays various operation screens on the display 101 so as to allow the operator to input through the operation screen for controlling operations of the automatic analyzer 100.

The operation section 102 is connected to a main body of the analyzer via a connection cable 108. The main body of the analyzer includes a sample charging section 103 for accommodating a sample container 109, a first analysis section (104) and a second analysis section (105) in which the sample dispensed into a reaction vessel reacts with the reagent for analysis, a sample storage section 106 for storing the analyzed sample, and a sample carrier section 107 for carrying the sample container 109. The sample carrier section 107 includes a lane for transversely linking the sample charging section 103, the first analysis section (104), the second analysis section (105), and the sample storage section 106. The sample container 109 is carried while being held in a holder (cup, rack and the like).

The first analysis section (104) includes a sample dispensation mechanism 111 for distributing the sample (specimen) from the sample container 109, a reaction disk 114 for circumferentially accommodating the reaction vessel in which the dispensed sample is reacted with the reagent, a reagent disk 115 capable of accommodating a plurality of reagent bottles 116 while rotating in accordance with the inspection item, a first reagent dispensation mechanism (112), and a second reagent dispensation mechanism (113) each for dispensing the reagent distributed from the reagent bottle 116 into the reaction vessel on the reaction disk 114. Generally, two types of reagent, that is, the first reagent and the second reagent are used for the normal inspection. Accordingly, the first analysis section (104) includes two reagent dispensation mechanisms. The reaction disk 114 includes a reaction tank filled with water where the reaction vessel is immersed and stored. As the reaction vessel is immersed in water of the reaction tank, the temperature at which the sample is reacted with the reagent in the reaction vessel is kept constant. The second analysis section (105) has the similar mechanism to that of the first analysis section (104).

The automatic analyzer 100 is configured to use a sample dispensation mechanism 111, a reaction vessel mounted on a reaction disk 114, a first reagent dispensation mechanism (112), and a second reagent dispensation mechanism (113) repeatedly for the plurality of measurements. The automatic analyzer 100 is cleaned (maintained) with pure water for the purpose of eliminating the influence as described below.

To prevent the component of the sample collected from a patient from influencing measurement of the sample collected from another patient.

To prevent the component of the reagent from influencing measurements between one item and another.

Execution of the maintenance specified by the instruction manual is indispensable for removing impurities accumulated in use. Exchange of water in the reaction tank is one of the maintenance operations. The exchange of water in the reaction tank is performed by draining water filled in the reaction tank so that the reaction tank is newly filled with water again. Drainage and water supply may be repeatedly performed in order to remove impurities inside the reaction tank.

(1-2) Maintenance Execution Instruction Screen

Figure 2:
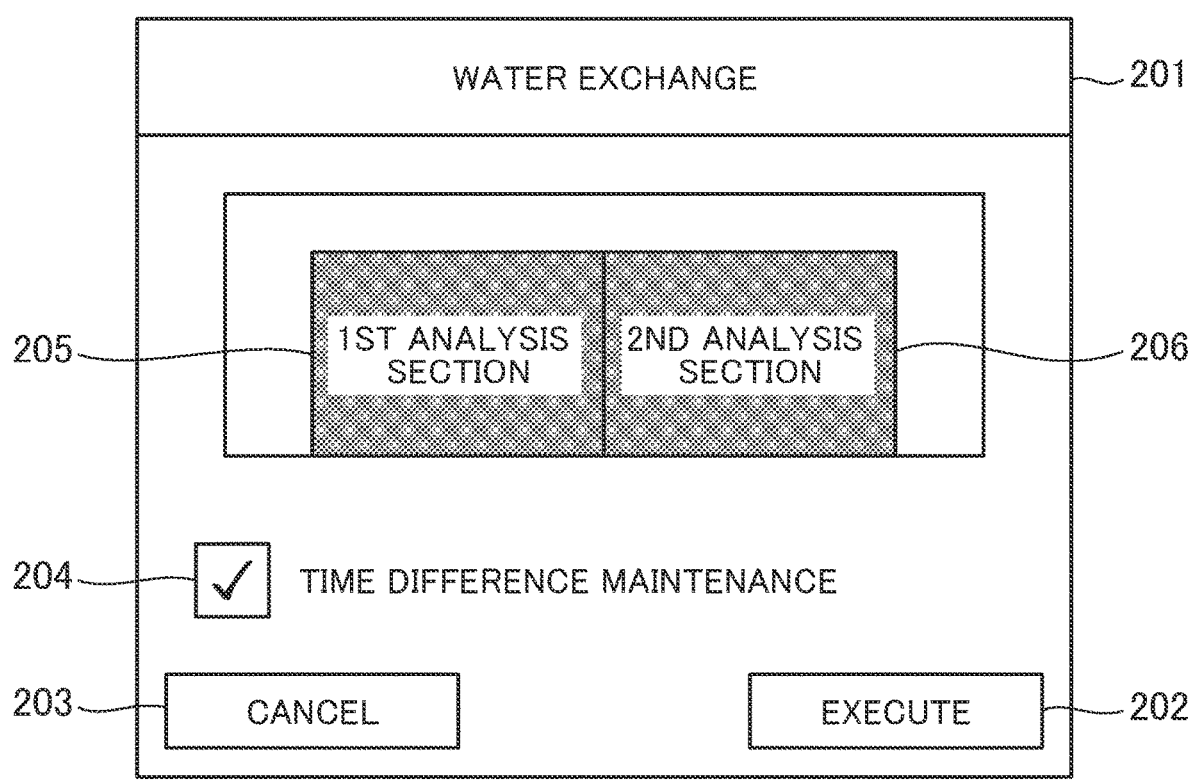
FIG. 2 is a view showing an exemplary maintenance execution instruction screen.

FIG. 2 shows an exemplary screen (maintenance execution instruction screen 201) for instructing exchange of water in the reaction tank. The maintenance execution instruction screen 201 displays an execution button 202 to instruct "execution" of the maintenance, a cancel button 203 to close the screen without executing the maintenance, a first analysis section button 205 and a second analysis section button 206 for designating the analysis section to be maintained, and a time difference maintenance designation checkbox 204. The operation for executing the maintenance will be changed depending on the checked or unchecked state of the time difference maintenance designation checkbox 204.

(1-3) Maintenance Operation (1-3-1) Normal State

Figure 3:
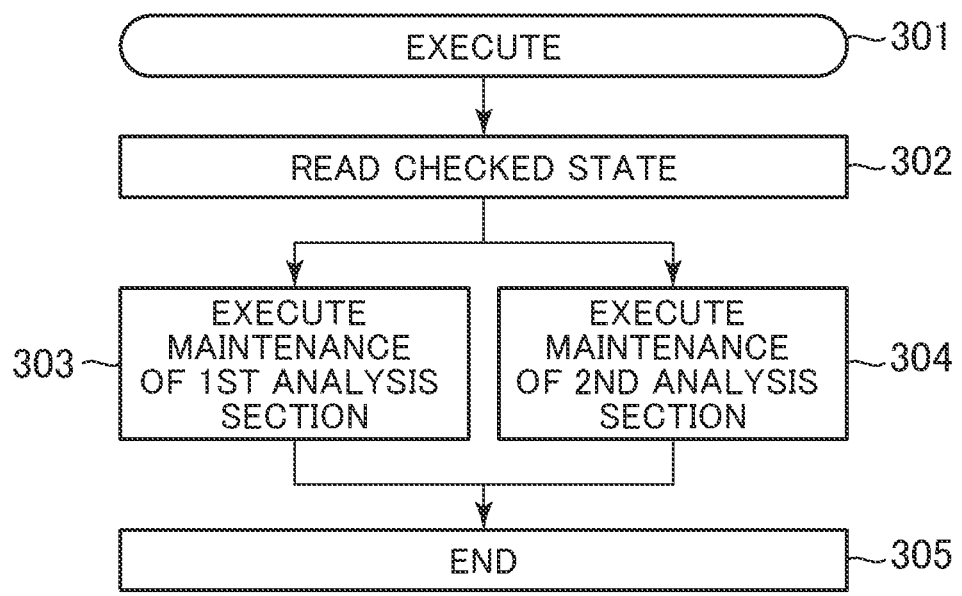
FIG. 3 is a flowchart representing process steps to be executed if the checkbox corresponding to the time difference maintenance is unchecked (normal case).

FIG. 3 is a flowchart representing process steps to be executed if the time difference maintenance designation check box 204 (FIG. 2) is unchecked. Detecting depression of the execution button 202 (execution button depression step 301), the control section (CPU) executes reading step 302 with respect to the checked state of the time difference maintenance designation checkbox 204.

FIG. 3 represents the process steps to be executed if the checkbox is unchecked. The control section (CPU) executes maintenance execution step 303 for the first analysis section simultaneously with maintenance execution step 304 for the second analysis section. In the maintenance execution step 303 for the first analysis section, the control section (CPU) sends an instruction to exchange water in the reaction tank to the first analysis section (104). Similarly in the maintenance execution step 304 for the second analysis section, the control section (CPU) sends an instruction to exchange water in the reaction tank to the second analysis section (105).

A simultaneous operation of the two analysis sections 104, 105 requires the automatic analyzer 100 to feed water by the amount twice the water consumed by the single analysis section all at once. If the feedable water amount is smaller than the amount of water consumed by the two analysis sections, the automatic analyzer 100 sounds an alarm for interrupting the maintenance. At the end of the maintenance step 303 for the first analysis section (104) and the maintenance step 304 for the second analysis section (105), the control section (CPU) proceeds to maintenance end step 305 to end the maintenance.

(1-3-2) Time Difference Maintenance

Figure 4:
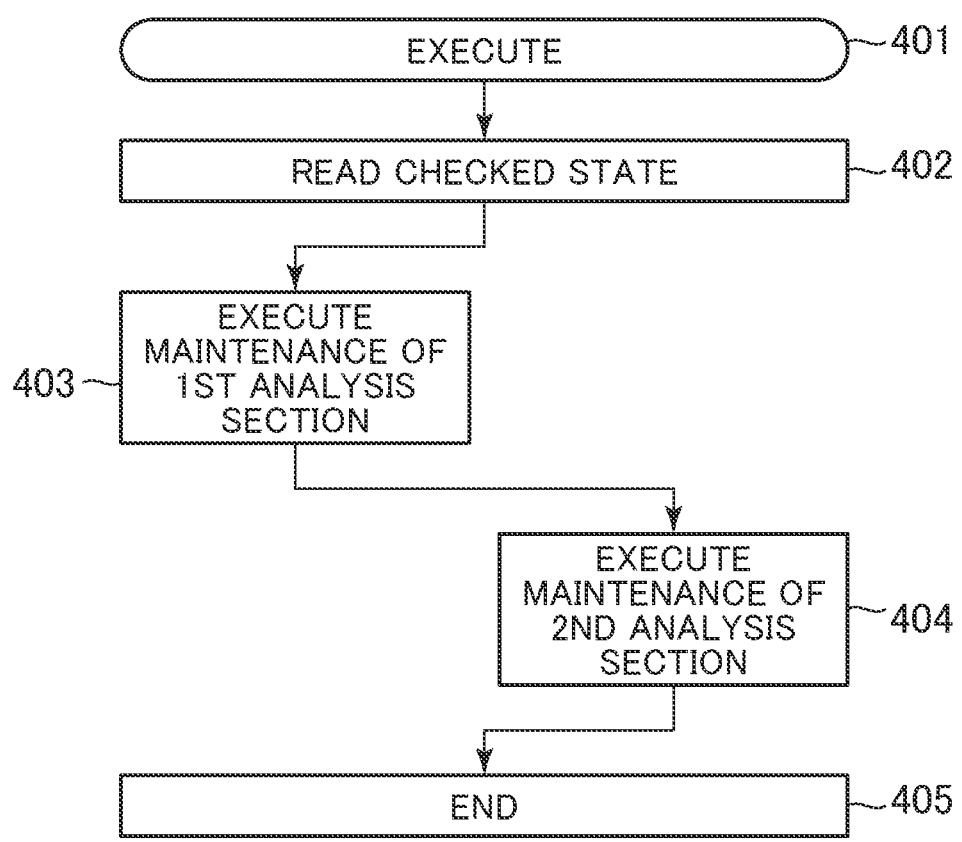
FIG. 4 is a flowchart representing process steps to be executed if the checkbox corresponding to the time difference maintenance is checked.

FIG. 4 is a flowchart representing process steps to be executed if the time difference maintenance designation checkbox 204 (FIG. 2) is checked. Detecting depression of the execution button 202 (execution button depression step 401), the control section (CPU) executes reading step 402 with respect to the checked state of the time difference maintenance designation checkbox 204.

FIG. 4 represents the process steps to be executed if the checkbox is checked. The control section (CPU) executes the maintenance for the analysis sections one by one with a time difference. Referring to FIG. 4, the control section (CPU) first executes maintenance execution step 403 for the first analysis section (104), and sends the instruction to exchange water in the reaction tank to the first analysis section (104). At the end of exchanging water in the tank for the first analysis section (104), the control section (CPU) executes maintenance execution step 404 for the second analysis section (105), and sends the instruction to exchange water in the reaction tank to the second analysis section (105).

In the case of the time difference maintenance, the analysis sections will be operated one by one. In spite of the structure including two analysis sections 104 and 105, the maximum water consumption required for the water exchange maintenance is equivalent to the amount of water consumed by the single analysis section. At the end of water exchange in the reaction tank for the second analysis section (105), the control section (CPU) proceeds to maintenance end step 405 to end the maintenance.

(1-3-3) Partial Time Difference Maintenance

Figure 5:
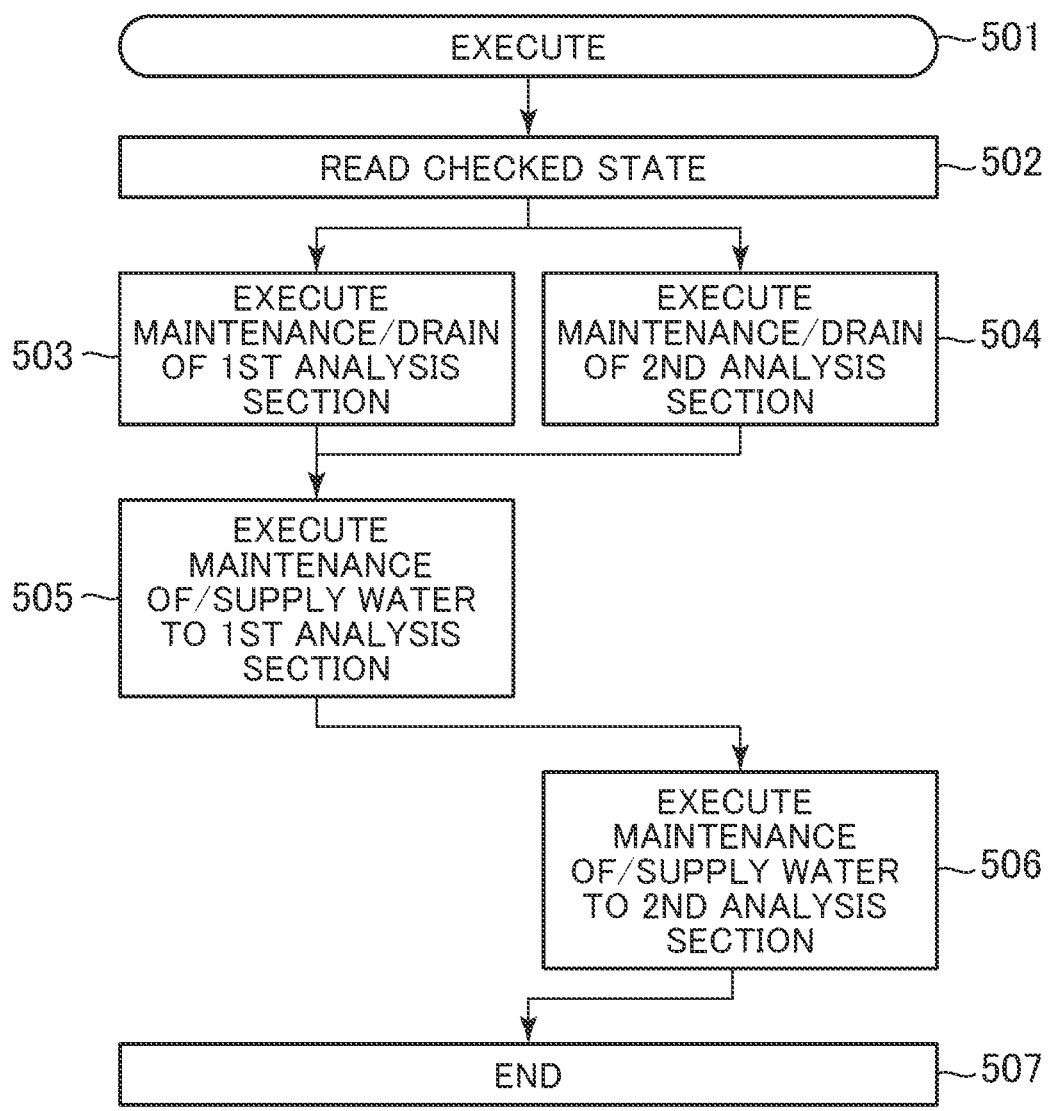
FIG. 5 is a flowchart representing process steps to be executed by segmenting the maintenance work if the checkbox corresponding to the time difference maintenance is checked.

The time difference maintenance as shown in FIG. 4 is executed through water exchange maintenance for the two analysis sections 104 and 105 successively. As a result, the processing time is twice longer than the time for the water exchange maintenance in the normal state as shown in FIG. 3. FIG. 5 represents process steps for the maintenance operation requiring the time shorter than the time difference maintenance as shown in FIG. 4 by simultaneously executing operations only for some parts of the analysis sections requiring no water supply.

Detecting depression of the execution button 202 (execution button depression step 501), the control section (CPU) executes reading step 502 to read the checked state of the time difference maintenance designation checkbox 204.

FIG. 5 represents process steps to be executed if the checkbox is checked. The control section (CPU) executes a first half step 503 (that is, the step using no water) of the maintenance execution process for the first analysis section (104), and sends the instruction to drain water to the first analysis section (104). Simultaneously, the control section (CPU) executes a first half step 504 (that is, the process using no water) of the maintenance execution process for the second analysis section (105), and sends the instruction to drain water to the second analysis section (105).

At the end of the draining process for both the first analysis section (104) and the second analysis section (105), the control section (CPU) starts executing a second half step 505 (that is, process using water) of the maintenance process for the first analysis section (104), and sends the instruction to supply water to the first analysis section (104).

At the end of water supply to the first analysis section (104), the control section (CPU) starts executing a second half step 506 (that is, process using water) of the maintenance execution process for the second analysis section (105), and sends the instruction to supply water to the second analysis section (105).

At the end of the water supply to the second analysis section (105), the control section (CPU) proceeds to maintenance end step 507 to end the maintenance. Since the maintenance operation shown in FIG. 5 is executed through water drainage for the first analysis section (104) and the second analysis section (105) simultaneously, the time required for the drainage may be reduced to the one taken for draining the single analysis section. The total operation time for maintenance as shown in FIG. 5 may be shorter than the total operation time as shown in FIG. 4.

(2) Example 2

Figure 6:
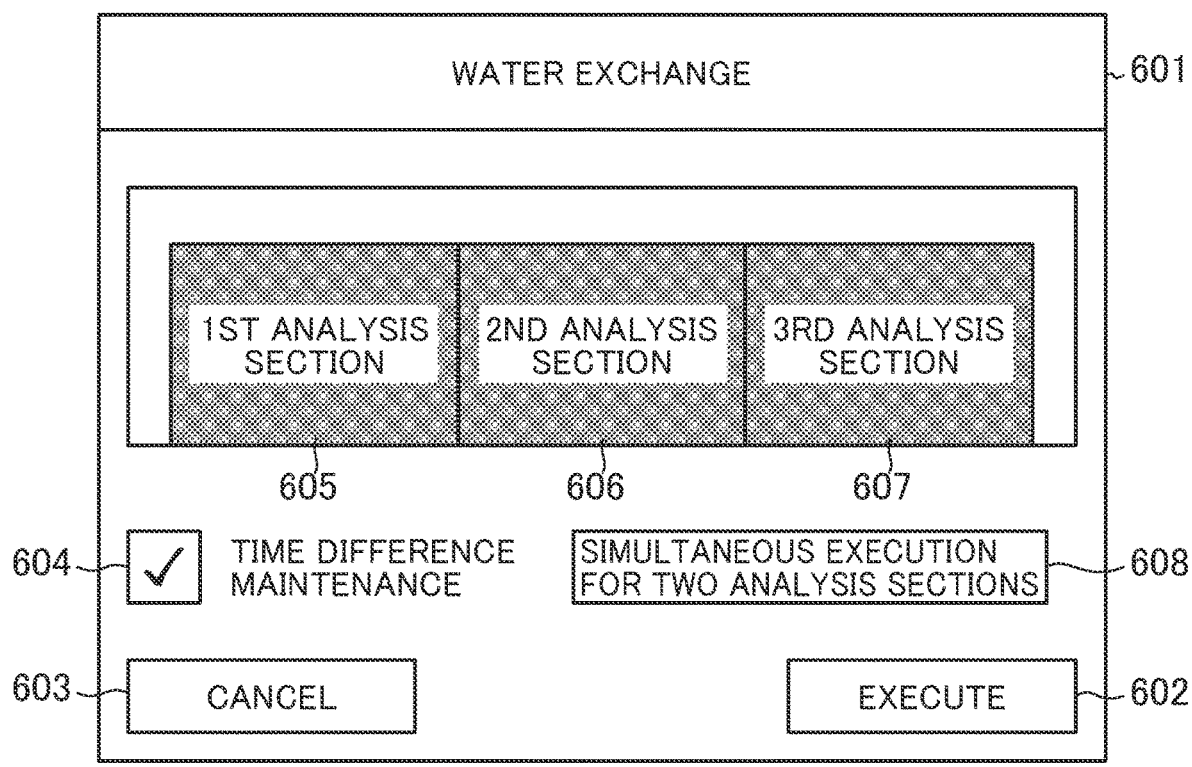
FIG. 6 is a view showing an exemplary maintenance execution instruction screen for the automatic analyzer including three analysis sections.

This example will be described with respect to the automatic analyzer 100 including three or more analysis sections. FIG. 6 shows an exemplary maintenance execution instruction screen 601 according to this example. The maintenance execution instruction screen 601 displays an execution button 602 for instructing "execution" of the maintenance, a cancel button 603 for closing the screen without executing the maintenance, a first analysis section button 605, a second analysis section button 606, and a third analysis section button 607 for designating the analysis section to be maintained, a time difference maintenance designation checkbox 604, and a menu box 608 for selecting the simultaneous execution range. The time difference maintenance designation checkbox 604 has the same function as that of the time difference maintenance designation checkbox 204 as shown in FIG. 2.

In Example 1, all the analysis sections of the automatic analyzer 100 (that is, analysis sections 104, 105) were applicable to the time difference maintenance range. In this example, the analysis section range (applicable range) for executing the time difference maintenance may be selected by inputting through the menu box 608. FIG. 6 shows the state where two out of the three analysis sections are selected as the applicable range for simultaneous execution. The menu box 608 allows selection of the analysis section range (applicable range) for executing the time difference maintenance from the menu including "execution only for the single analysis section", and "simultaneous execution for two analysis sections".

If the operator selects the "execution only for the single analysis section", the control section (CPU) executes the water exchange maintenance for the three analysis sections one by one sequentially. If the operator selects the "simultaneous execution for two analysis sections", the control section (CPU) executes the water exchange maintenance for two of the three analysis sections simultaneously, and further executes the water exchange maintenance for the third analysis section after finishing the simultaneous water exchange maintenance.

Figure 7:
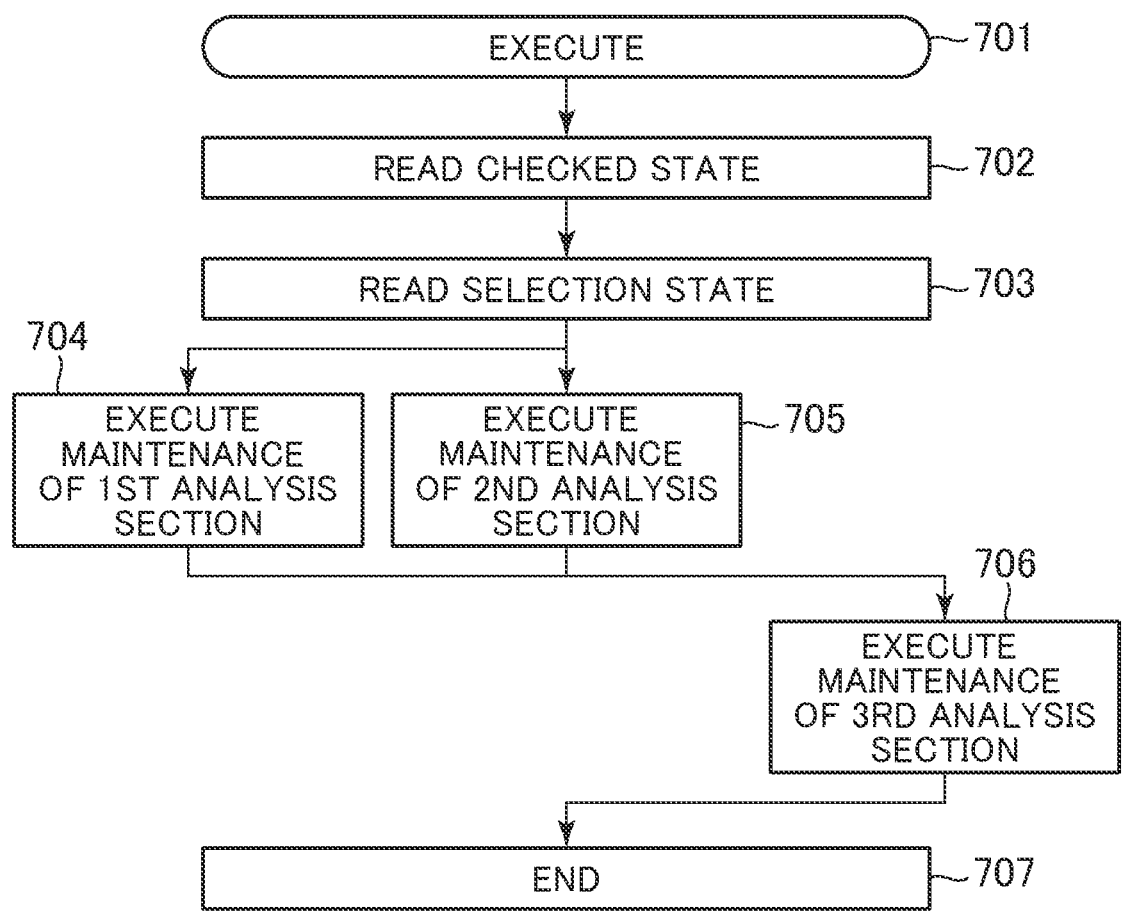
FIG. 7 is a flowchart representing process steps to be executed if the checkbox corresponding to the time difference maintenance is checked for the automatic analyzer including three analysis sections.

FIG. 7 represents the time difference maintenance process steps to be executed when the operator checks the time difference maintenance designation checkbox 604, and selects the "simultaneous execution for two analysis sections" from the menu box 608.

Upon detecting depression of the execution button 602 (execution button depression step 701), the control section (CPU) executes a step 702 for reading the checked state of the time difference maintenance designation checkbox 604. If it is checked, the control section (CPU) executes a step 703 for reading the selection state of the menu box 608 so as to read the applicable range of the analysis sections subjected to the simultaneous execution of water exchange maintenance.

FIG. 7 represents process steps to be executed upon selection to the "simultaneous execution for two analysis sections". The control section (CPU) instructs to execute a maintenance step 704 for the first analysis section and a maintenance step 705 for the second analysis section simultaneously. That is, the control section (CPU) sends the respective instructions to exchange water in the reaction tank to the first analysis section (104) and the second analysis section (105) simultaneously.

At the end of water exchange both for the first analysis section (104) and the second analysis section (105), the control section (CPU) instructs execution of a maintenance execution step 706 for the third analysis section, and sends the instruction to exchange water in the reaction tank to the third analysis section (not shown). At the end of the maintenance execution step 706 for the third analysis section, the control section (CPU) proceeds to maintenance end step 707 to end the maintenance.

If the "execution only for the single analysis section" is selected from the menu box 608, the control section (CPU) instructs execution of the water exchange maintenance for three analysis sections one by one sequentially like the way as shown in FIG. 4. If the time difference maintenance designation checkbox 604 is not checked, the control section (CPU) instructs simultaneous execution of the water exchange maintenance for the three analysis sections.

The above-described mechanism applies to the automatic analyzer including four or more analysis sections. In this case, the maximum number of the analysis sections designable from the menu box 608 may be obtained by subtracting 1 from the total number of the analysis sections. The control section (CPU) controls the schedule for executing the water exchange maintenance in accordance with the number of the analysis sections selected by the operator.

A certain type of automatic analyzer including a plurality of analysis sections may be configured to control not to operate some of the analysis sections. In this case, the above-described mechanism is applicable only to the executable analysis sections. If the automatic analyzer 100 includes three analysis sections, and is set so as not to operate the first analysis section, the control section (CPU) instructs execution of the water exchange maintenance only for two analysis sections, that is, the second analysis section and the third analysis section simultaneously. The instruction is the same as that of the case where the "simultaneous execution for two analysis sections" is selected from the menu box 608 in addition to the above-described condition. If the "execution only for the single analysis section" is selected from the menu box 608, the control section (CPU) executes the water exchange maintenance for the third analysis section after finishing the water exchange maintenance for the second analysis section.

Referring to FIG. 6, the time difference maintenance designation checkbox 604 and the menu box 608 are displayed on the maintenance execution instruction screen 601. However, they may be displayed on another screen. In such a case, for execution of the water exchange maintenance, the control section (CPU) reads the information instructed on the respective screens from the storage section so as to determine the number of the analysis sections to be subjected to execution of the simultaneous maintenance operation.

(3) Example 3

In the foregoing examples, the operator instructs whether or not the time difference maintenance is to be executed through the maintenance execution instruction screens 201, 601. Alternatively, the control section (CPU) may be configured to automatically set whether or not the time difference maintenance is to be executed based on the "water supply amount" and "required water amount" preliminarily set by the operator.

Figure 8:
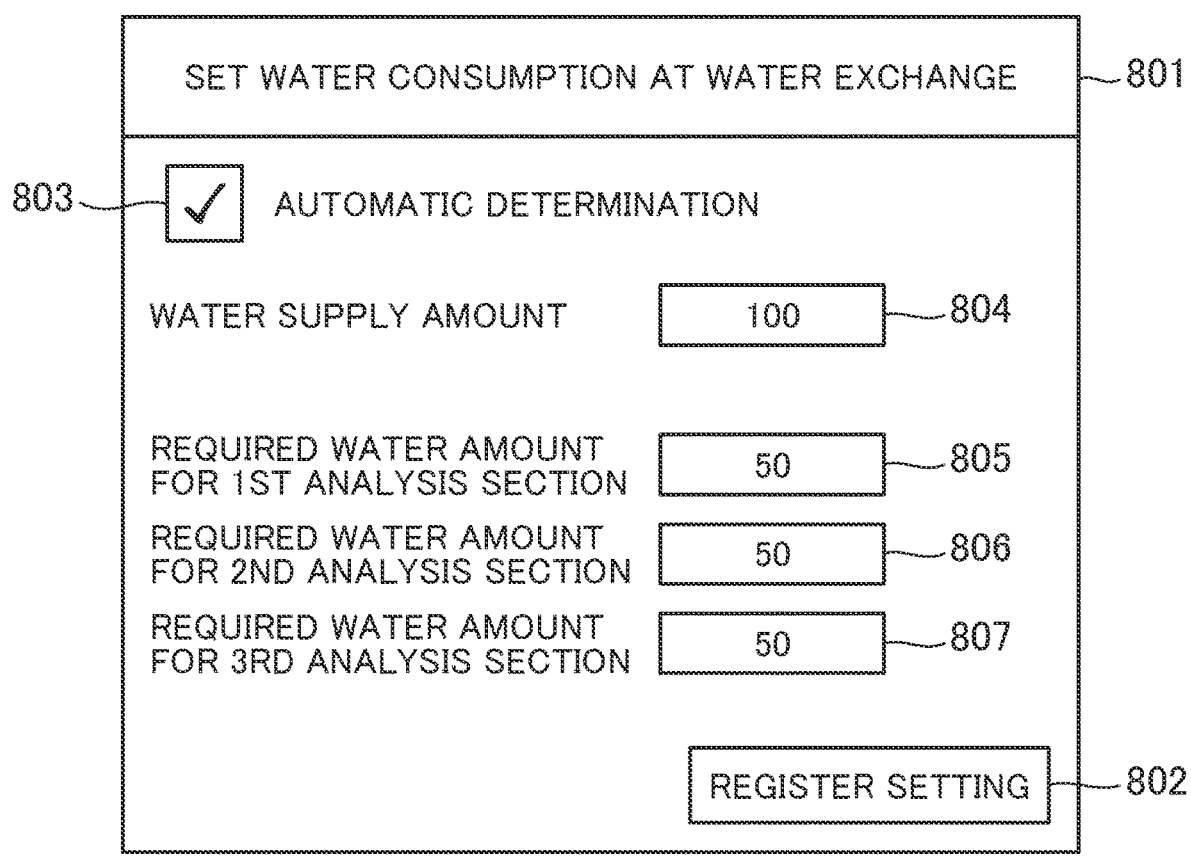
FIG. 8 is a view showing an exemplary screen for setting the amount of water externally supplied to the automatic analyzer, and water consumption required for the respective analysis sections.

FIG. 8 shows an exemplary screen 801 for setting water consumption at water exchange according to this example. The screen 801 for setting water consumption at water exchange displays a setting registration button 802 for registering the value input through the screen, a checkbox 803 (checkbox for enabling automatic determination) for instructing whether or not the automatic determination is executed based on the value set through the screen, a water supply amount input area 804 for inputting an amount value of water feedable to the automatic analyzer per unit time, an input area 805 (area for inputting a required water amount for the first analysis section) for inputting an amount value of water (required amount) for the first analysis section per unit time, an input area 806 (area for inputting a required water amount for the second analysis section) for inputting an amount value of water (required amount) for the second analysis section per unit time, and an input area 807 (area for inputting a required water amount for the third analysis section) for inputting an amount value of water (required amount) for the third analysis section. The operator sets and registers "water supply amount" and "required water amount" through the screen 801 for setting water consumption at water exchange as well as execution/non-execution of the automatic determination.

Firstly, the control section (CPU) judges whether or not the checkbox 803 for enabling automatic determination has been checked. If it is checked, the control section (CPU) automatically determines whether or not the time difference maintenance is to be executed based on the set and registered value.

Figure 9:
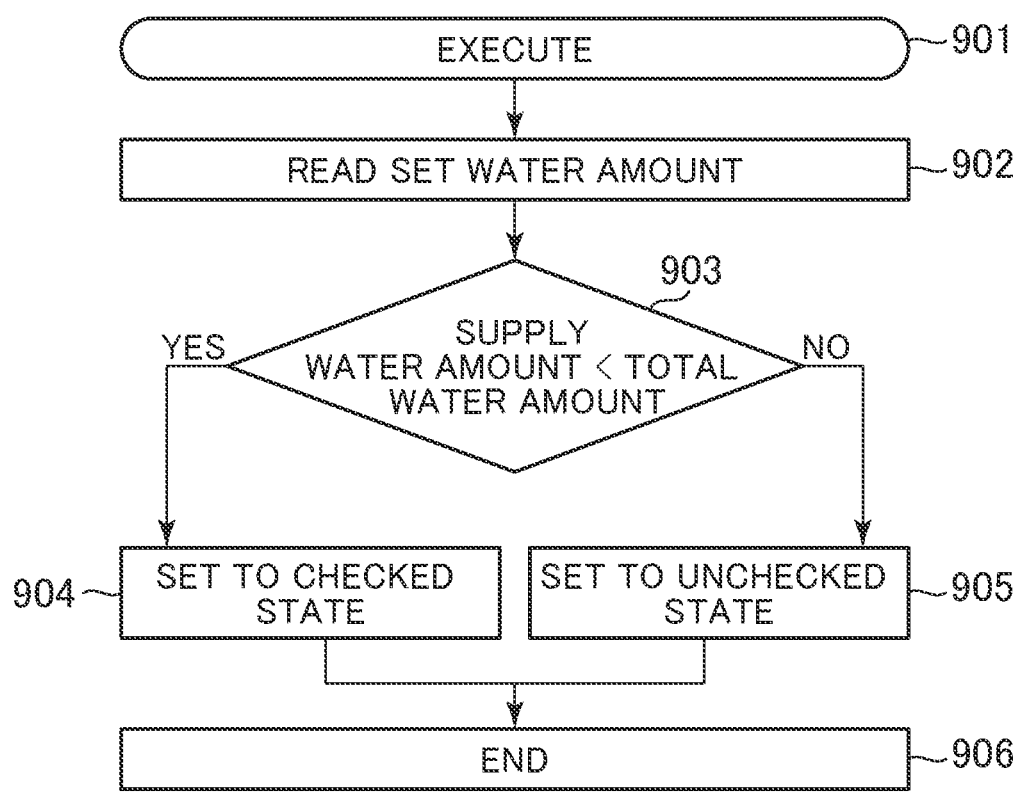
FIG. 9 is a flowchart representing process steps for automatically setting execution or non-execution of the time difference maintenance based on the information set through the screen as shown in FIG. 8.

FIG. 9 is a flowchart representing process steps to be executed if the checkbox 803 for enabling automatic determination has been checked. If the checkbox 803 for enabling automatic determination has been checked, the control section (CPU) starts execution of automatic execution step 901. The control section (CPU) then executes step 902 for reading the set water amount. In this step, the control section (CPU) reads values of the water amounts set in the water supply amount input area 804, in the input area 805 for inputting required water amount for the first analysis section, in the input area 806 for inputting required water amount for the second analysis section, and in the input area 807 for inputting required water amount for the third analysis section from the not shown storage section.

At the end of reading the set water amount values, the control unit (CPU) obtains the relationship between the "water supply amount" and the "total water amount" (step 903). The "total water amount" denotes the total value of a value of the required amount of water set in the input area 805 for inputting required water amount for the first analysis section, a value of the required amount of water set in the input area 806 for inputting required water amount for the second analysis section, and a value of the required amount of water set in the input area 807 for inputting required water amount for the third analysis section. The total value is calculated by the control section (CPU).

If the "water supply amount" is smaller than the "total water amount", the control section (CPU) sets so that the checkbox corresponding to the time difference maintenance is "checked" (step 904). Meanwhile, if the "water supply amount" is equal to or larger than the "total water amount", the control section (CPU) sets so that the checkbox corresponding to the time difference maintenance is "unchecked" (step 905). After setting, the control section (CPU) ends the determination step (step 906).

At the end of the above-described determination step, the control section (CPU) executes the water exchange maintenance in accordance with the checked state of the time difference maintenance. If the checkbox corresponding to the time difference maintenance is "checked", the control section (CPU) determines to combine the analysis sections so that the total amount of required water does not exceed the water supply amount, and executes the water exchange maintenance for the combined analysis sections simultaneously. Thereafter, the control section further executes the water exchange maintenance for the remaining analysis section. Meanwhile, if the checkbox corresponding to the time difference maintenance is "unchecked", the control section (CPU) executes the water exchange maintenance for all the analysis sections simultaneously as shown in FIG. 3.

(4) Other Examples

The present invention is not limited to the above-described examples, but includes various modifications. For example, the above-described examples have been described in detail for easy understanding of the present invention. Therefore, all the components as described above do not have to be necessarily provided. It is possible to replace a part of the structure of one example with the structure of another example. It is also possible to add the structure of an example to that of another example. It is still possible to eliminate the part of the structure of each of the examples.

It is possible to partially or entirely implement the above-described structure, function, processing section, processing means and the like by means of hardware, for example, by designing with the integrated circuit. It is also possible to implement the above-described structures and functions (by means of software) through interpretation and execution of the program by which the processor executes the respective functions. The information of the program, table, file and the like for implementing the respective functions may be stored in the storage device such as the memory, the hard disk, and the SSD (Solid State Drive), or the recording medium such as the IC card, the SD card, the DVD and the like. The control lines and information lines regarded as necessary for the explanation are shown. It is to be understood that those lines do not necessarily indicate all the control lines and the information lines necessary for the product. Actually, almost all the components may be considered as being interconnected with one another.

LIST OF REFERENCE SIGNS

100: automatic analyzer,
101: display,
102: operation section,
103: sample charging section,
104: first analysis section,
105: second analysis section,
106: sample storage section,
107: sample carrier section,
108: connection cable,
109: sample container,
111: sample dispensation mechanism,
112: first reagent dispensation mechanism,
113: second reagent dispensation mechanism,
114: reaction disk,
115: reagent disk,
116: reagent bottle,
201: maintenance execution instruction screen,
202: execution button,
203: cancel button,
204: time difference maintenance designation checkbox,
205: first analysis section button,
206: second analysis section button,
601: maintenance execution instruction screen,
602: execution button,
603: cancel button,
604: time difference maintenance designation checkbox,
605: first analysis section button,
606: second analysis section button,
607: third analysis section button,
608: menu box,
801: screen for setting water consumption at water exchange,
802: setting registration button,
803: checkbox for enabling automatic determination,
804: water supply amount input area,
805: input area for inputting required water amount for the first analysis section,
806: input area for inputting required water amount for the second analysis section,
807: input area for inputting required water amount for the third analysis section

The invention claimed is:

1. An automatic analyzer comprising:
a plurality of analysis sections for sample analysis, each comprising a reaction disk with a reaction tank, each reaction tank being configured to exchange water supplied from outside of the automatic analyzer to fill each reaction tank;
a display device; and
a processor executing a program for controlling operations of the analysis sections,
wherein the processor is programmed to:
control the display device to display a maintenance execution instruction screen for designating whether to execute time difference maintenance using water for the plurality of analysis sections or to execute simultaneous maintenance for at least two of the analysis sections; and
upon receiving both a designation to execute the time difference maintenance and a designation to execute the simultaneous maintenance for the at least two of the analysis section, execute the simultaneous maintenance using water for the at least two analysis sections and switch to the time difference maintenance to sequentially execute the maintenance using water for remaining ones of the analysis sections other than the at least two of the analysis sections for which simultaneous maintenance is executed.

2. The automatic analyzer according to claim 1, wherein the processor is further programmed to:
in the case of receiving the designation to execute the simultaneous maintenance and not receiving the designation for time difference maintenance, simultaneously execute the maintenance using water for all of the analysis sections.

3. The automatic analyzer according to claim 1, wherein the maintenance is water exchange maintenance where water for the plurality of analysis sections is exchanged.

4. The automatic analyzer according to claim 1, wherein the processor is further programmed to:
in the case of receiving the designation to execute the time difference maintenance and not receiving the designation for simultaneous maintenance, serially execute the maintenance using water for all of the analysis sections.

* * * * *